US006302687B1

(12) United States Patent
King

(10) Patent No.: US 6,302,687 B1
(45) Date of Patent: Oct. 16, 2001

(54) APPLIANCE AND METHOD FOR MANDIBULAR WIDENING BY SYMPHYSEAL DISTRACTION OSTEOGENESIS

(76) Inventor: John W. King, 5921 Harbour La., Suite 300, Midlothian, VA (US) 23112

( * ) Notice: Subject to any disclaimer, the term of this patent is extended or adjusted under 35 U.S.C. 154(b) by 0 days.

(21) Appl. No.: 09/847,171

(22) Filed: May 3, 2001

(51) Int. Cl.[7] ............................... A61C 3/00; A61C 5/00
(52) U.S. Cl. ................... 433/7; 433/18; 433/215
(58) Field of Search ...................... 433/6, 7, 18, 215

(56) References Cited

U.S. PATENT DOCUMENTS 2,086,656 * 7/1937 Woodward ...................... 433/18 X
2,481,177 * 9/1949 Tofflemire ...................... 433/18 X
4,482,318 * 11/1984 Forster ................................ 433/7
5,002,485 * 3/1991 Aagesen ............................. 433/7
5,564,920   10/1996 Klapper et al. .

* cited by examiner

Primary Examiner—Nicholas D. Lucchesi
(74) Attorney, Agent, or Firm—Norman B. Rainer

(57) ABSTRACT

Mandibular widening by symphyseal distraction osteogenesis is accomplished with the use of an appliance having first and second elongated support arms and an intervening displacement mechanism which, by rotation upon a horizontal axis, performs in the manner of a turnbuckle to force the arms apart. Lower apertures on the arms are attached to the mandibular bone, and upper apertures on the arms are attached to the teeth. Following a mid-symphyseal osteotomy and a latency period, the displacement mechanism is rotated according to a precise schedule to achieve widening of the lower jaw.

16 Claims, 4 Drawing Sheets

APPLIANCE AND METHOD FOR MANDIBULAR WIDENING BY SYMPHYSEAL DISTRACTION OSTEOGENESIS

BACKGROUND OF THE INVENTION

1. Field of the Invention

This invention concerns a mandibular distraction apparatus and its manner of use, and more particularly relates to an intraoral mandibular distraction apparatus for temporary attachment to the teeth and bone to produce osteogenesis by patient manipulation preparatory to an orthodontic remediation.

2. Description of the Prior Art

In a series of studies published by G. A. Ilizarov beginning in 1988, techniques were described for lengthening endochondral bones and the surrounding soft tissue matrix. In particular, it was shown that the genesis of new bone tissue between facing surfaces of a newly cut bone is dependent upon tension-stress effects associated with the rate and frequency of distraction, namely the forced separation of said facing surfaces.

In a series of studies published since 1997 by W. H. Bell and others, it was shown that the osteogenesis principles elucidated by Ilizarov can be facilitated with intraoral appliances to achieve mandibular widening by symphyseal distraction. Such technique has been found useful in facilitating orthodontic remediation of mandibular crowding and other conditions. The appliance employed by Bell, now marketed as DynaForm™ by Stryker Leibinger Gmb H of Freiburg, Germany, is comprised of two frames interconnected by an advancing screw rotatively held by a fixed yoke mounted upon paired slide posts. Each frame is comprised of a rigid bar base and superior and inferior elongated arms orthogonally emergent from said base and terminating in distal extremities directed away from said bases. The base of one of said frames functions a yoke moveable upon said screw and slide posts. The arms are bendable to match the patient's buccal mandibular contour, and securement forks or rings are crimped onto the distal extremities. When proper fitting has been achieved, the extremities of the upper arms are secured to mandibular teeth, and the lower extremities are secured to mandibular bone.

Following installation of the Bell appliance bridging the site of osteotomy, carefully controlled distraction to distances of 7 to 12 mm. is accomplished by an activation tool in the nature of a specialized screwdriver employed by the dentist to engage the horizontally directed head of the screw, and rotate the screw.

An intraoral palatal expansion device available from Orthodesign of Chicago, Ill. has been described by Liou, et. al. in the Journal of Craniofacial Surgery, Vol. 9, No. 6, pgs 564–71, Nov. 1998. The Orthodesign distractor is comprised of two laterally opposed arms and an intervening rotatable screw device in the nature of a turnbuckle having oppositely threaded screws telescopically interactive with a barrel-like body having a faceted central region. When emplaced, the arms attach to the bone of the mandible, and the screw device extends transmucosally within the vestibule of the mandible. Although the method of operation of the screw device is not disclosed by Liou, the distraction is presumably achieved by rotation of the barrel-like body of the turnbuckle, employing an open-ended hex wrench that engages the faceted central region.

It has been found, however, that bone-borne distraction appliances such as Liou's having only two attachment sites produce a V-shaped bone regenerate which is not as stable or desirable as a parallel regenerate, particularly in the case of symphyseal mandibular widening. It is further necessary that means be provided whereby the telescopic screw is caused to be parallel with the desired vector of distraction.

In order to achieve best osteogenesis results, a carefully prescribed rate of distraction is required, such as two 0.5 mm. increments/day. Such regimen is best achieved when the patient, parent or other caregiver can administer the prescribed rated of distraction at home.

It is accordingly an object of the present invention to provide an intraoral screw-activated appliance for mandibular widening by symphyseal distraction osteogenesis.

It is a further object of this invention to provide an appliance as in the foregoing object which will produce a substantially parallel bone regenerate.

It is another object of the present invention to provide an appliance of the aforesaid nature which can be patient-manipulated to achieve a carefully prescribed rate of distraction.

It is a still further object of this invention to provide an appliance of the aforesaid nature which allows for precise surgical placement such that the axis of screw rotation is parallel with the desired vector of distraction.

It is yet another object of the present invention to provide an appliance of the aforesaid nature having a low profile which results in greater comfort to the patient.

It is an additional object of this invention to provide an appliance of the aforesaid nature which is durable, reliable, and amenable to low cost manufacture.

It is a further object of the present invention to provide a method for mandibular widening employing the appliance of the aforesaid nature.

These objects and other objects and advantages of the invention will be apparent from the following description.

SUMMARY OF THE INVENTION

The above and other beneficial objects and advantages are accomplished in accordance with one aspect of the present invention by an intraoral appliance for mandibular widening by symphyseal distraction osteogenesis comprising:
  a) first and second elongated support arms of substantially equal length disposed in facing opposition, each arm comprised of upper and lower aperture-equipped extremities, and a central portion, and
  b) a displacement mechanism disposed between the central portions of said arms and interactive therewith, said mechanism comprising:
   1) a turning barrel elongated upon an axis of rotation between first and second end walls, and having a substantially circular cylindrical exterior surface provided with an annular gripping zone comprised of six flat facets in hexagonal array, said facets having instructive indicia,
   2) a machine screw having a proximal extremity attached to said first arm at said central portion and extending in threaded engagement with an axially centered threaded aperture in said first end wall, and terminating in a distal extremity located within said barrel, and
   3) a measuring tube slideably emergent from said second end wall upon said axis and extending to a proximal extremity attached to said second arm at said central portion, the distance of emergence of said rod being dependent upon the degree of rotational movement of said barrel.

BRIEF DESCRIPTION OF THE DRAWING

For a fuller understanding of the nature and objects of the invention, reference should be had to the following detailed description taken in connection with the accompanying drawing forming a part of this specification and in which similar numerals of reference indicate corresponding parts in all the figures of the drawing.

DESCRIPTION OF THE PREFERRED EMBODIMENT

Figure 1:
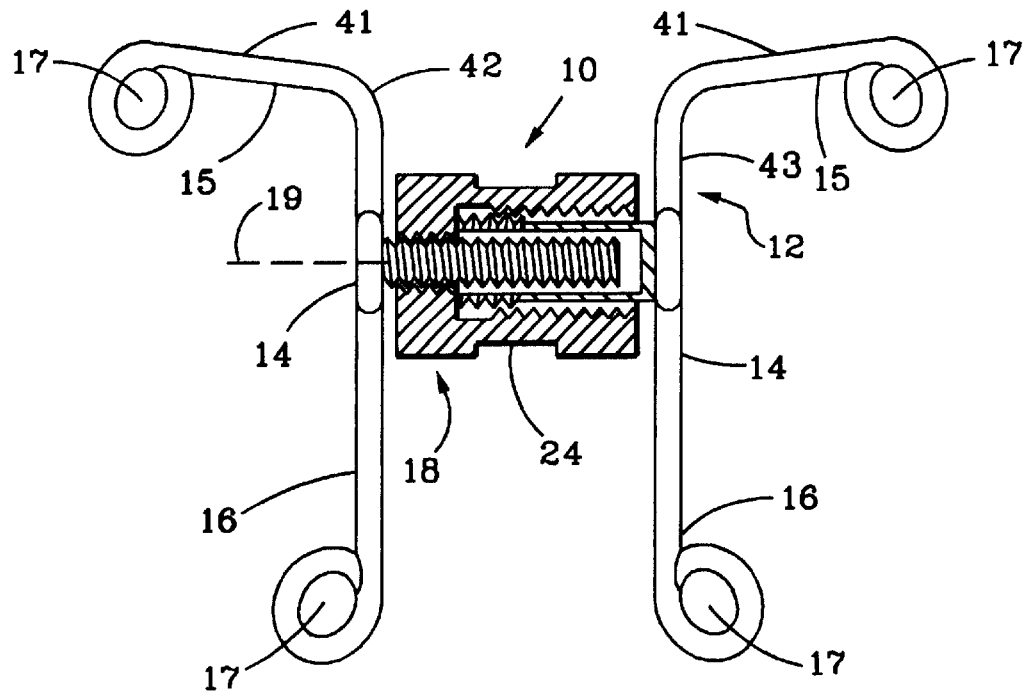
FIG. 1 is an enlarged vertical front sectional view of an embodiment of the distraction appliance of the present invention, shown in its starting position.
Figure 2:
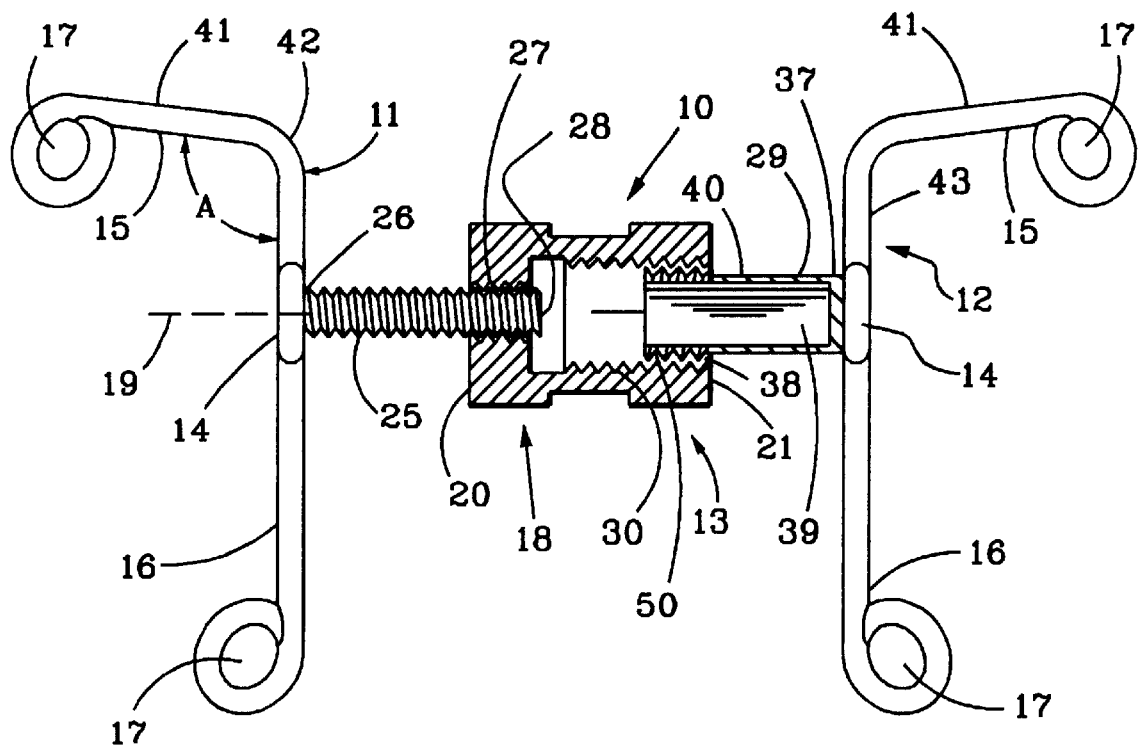
FIG. 2 is a view similar to FIG. 1 showing the appliance in its expanded, functional position.
Figure 3:
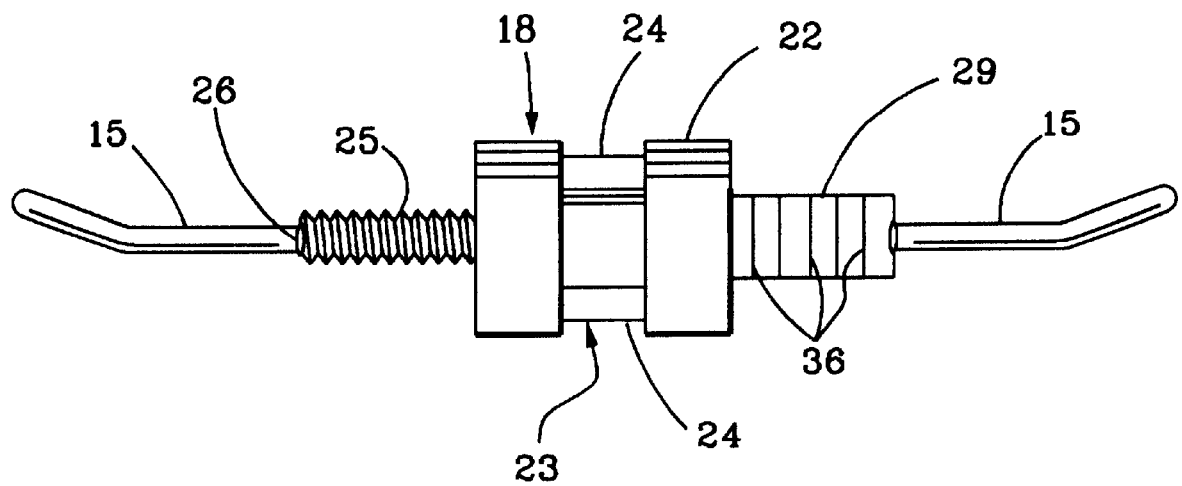
FIG. 3 is a top view of the embodiment of FIG. 2 following customized modification to fit a patient.
Figure 4:
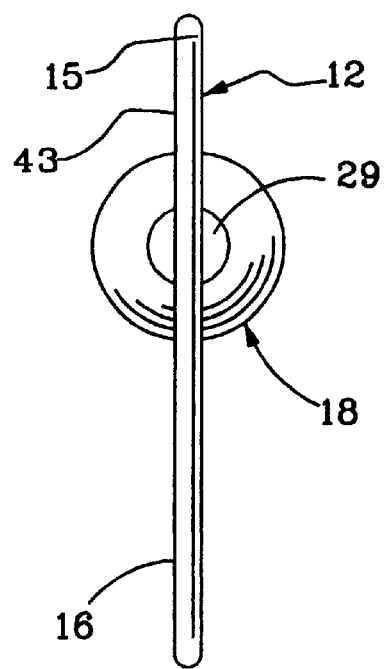
FIG. 4 is a right end view of the embodiment of FIG. 2.
Figure 5:
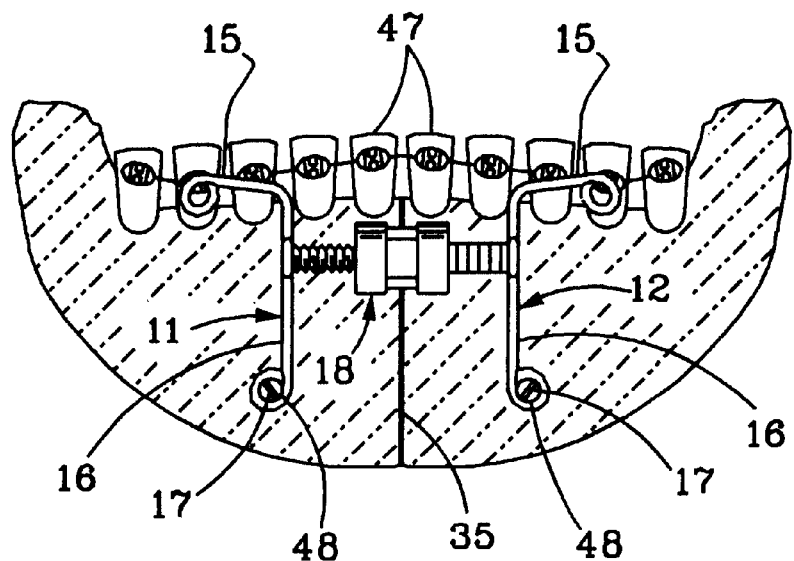
FIG. 5 is a front view of the embodiment of FIG. 2 following a distraction procedure and still installed on an orthodontic patient.
Figure 6:
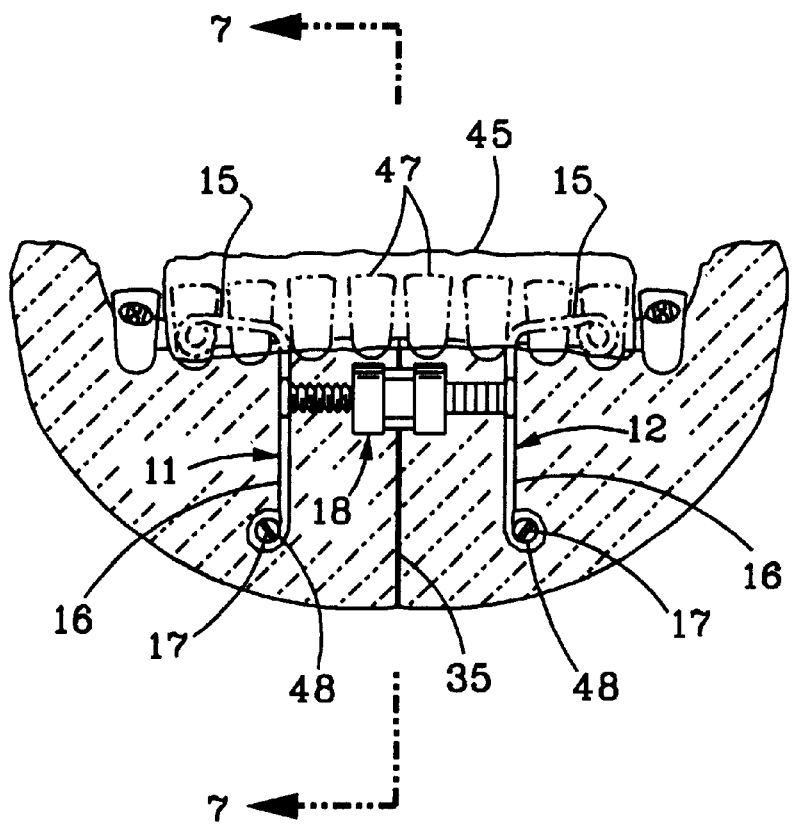
FIG. 6 is a front view of the embodiment of FIG. 5 provided with a removable index for establishing precise surgical placement of the appliance.
Figure 7:
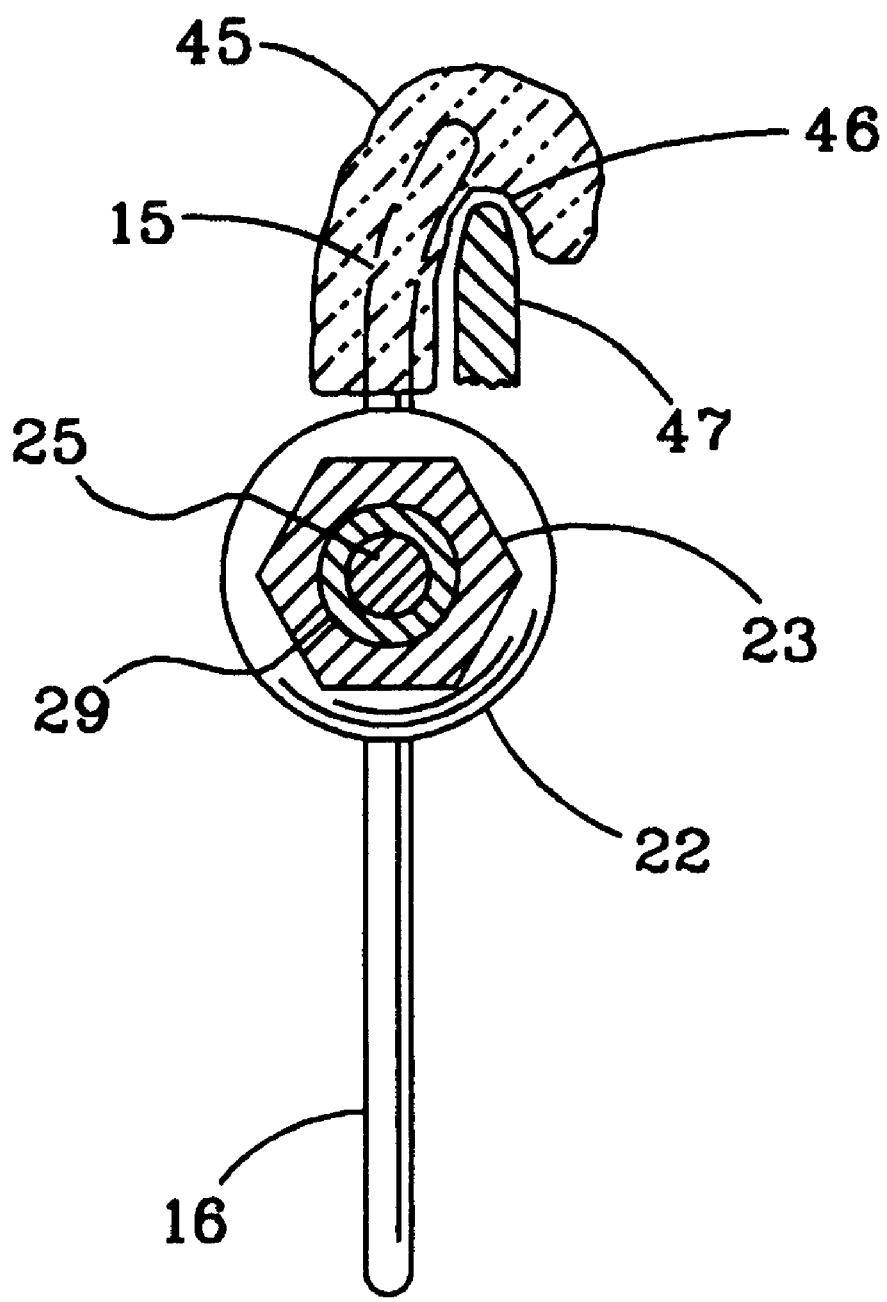
FIG. 7 is a sectional view taken in the direction of the arrows upon the line 7—7 of FIG. 6.

Referring now to FIGS. 1–7, an embodiment of the mandibular widening appliance 10 of the present invention is shown comprised of first and second elongated support arms 11 and 12, respectively, and intervening displacement mechanism 13.

Said support arms are of rigid but bendable metal construction, preferably fabricated as monolithic structures from metals such as stainless steel. The arms are of substantially equal length and mirror-image contour, having a central portion 14 and upper and lower portions 15 and 16, respectively, provided with apertures 17. The arms may be fabricated from wire stock, or may be otherwise fabricated to be of strong, thin construction. Apertures 17 may be fabricated by the bending of wire stock or by the drilling of ribbon stock or a molded piece. Apertures 17 may be either of full circular configuration, or of keyhole configuration having a partial circular configuration providing forklike access to the partial circle.

The support arms are configured such that lower portions 16 are substantially straight, and upper portions 15 are divergently directed by virtue of bending. The lengths of the upper and lower portions of each arm are substantially equal.

The exemplified embodiment of the displacement mechanism is comprised of a hollow turning barrel 18 elongated upon an axis of rotation 19 between first and second end walls 20 and 21, respectively. Barrel 18 has a substantially circular cylindrical exterior surface 22 provided with an annular gripping zone 23 having six flat facets 24 in a hexagonal array centered upon axis 19. The hexagonal configuration permits gripping by an open-headed hex wrench. The facets are provided with instructional indicia such as an arrow which indicates direction of rotation, and dots or numerals indicating extent of rotation.

A machine screw 25 having a proximal extremity 26 attached to the center portion of first arm 11 extends in threaded engagement with an axially centered threaded aperture 27 in first end wall 20, and terminates in a distal extremity 28 located within said barrel.

A hollow measuring tube 29 having a proximal extremity 37 attached to the center portion of second arm 12 extends to a distal extremity 50 in threaded engagement with internal threading 30 within barrel 18, and is slideably emergent from hole 38 in second end wall 21. The direction of threaded engagement of said measuring tube with barrel 18 is opposite to the direction of threaded engagement of machine screw 25 with said barrel. Accordingly, rotation of barrel 18 upon axis 19 produces a turnbuckle effect wherein rotation of the barrel in one direction will bring the moveable threaded members together, and rotation in the opposite direction will drive said members apart. A series of millimeter rulings 36 are disposed upon the cylindrical outer wall 40 of said measuring tube.

The diameter of machine screw 25 is sufficiently narrow to enter the hollow region 39 of measuring tube 29. By virtue of such manner of construction, the appliance of this invention has a very small overall length in its starting state, as shown in FIG. 1, and is capable of achieving distraction distances between 5 and 18 millimeters with accurate control by observation of the rulings 36 on measuring tube 29. The displacement mechanism 13 is generally similar to an orthodontic device disclosed in U.S. Pat. No. 5,564,920 for expanding the upper jaw.

The configuration of the divergent upper portions 15 of the arms with respect to the corresponding lower portions is such that said upper portions are bent at an angle A with respect to the lower portion. The value of angle A is between 90 and 115 degrees. The length of the laterally directed segment 41 of said upper portion, measured between the center of upper aperture 17 and the site of bending 42, is smaller than the length of the corresponding lower portion 16 measured between the center of the lower aperture and axis 19.

A lower segment 43 of each upper portion 15, will generally remain in straight alignment with the corresponding lower portion 16 of the arm. The length of said lower segment 43 will generally be shorter than the length of the corresponding laterally directed segment 41.

The appliance is employed in a multi-step treatment protocol involving the following phases:

1) Pre-surgical orthodontics
2) A mid-symphyseal osteotomy
3) A latency period
4) A distraction period
5) A consolidation period
6) Post-surgical orthodontics.

The first phase of pre-surgical orthodontics is similar to preparing a patient for conventional orthognathic surgery. If needed, the maxilla is expanded via rapid palatal expansion to its ideal width and arch form. It is advisable to diverge the roots of the teeth adjacent to the surgical site (usually the mandibular central incisors). However, a step-osteotomy may be performed between the central and lateral incisors, or even the lateral incisors and the canines. The surgery can be performed without opening space between the crowns in the surgery site.

The appliance is then custom fitted in a dental laboratory to a model based upon a lateral cephalometric x-ray, a P-A cephalometric x-ray and a mandibular alginate or PVS impression with a deep vestibular reflection in the anterior region. A submental vertex x-ray is also preferably provided. Such customization, achieved by accurate bending of arms 11 and 12, particularly the upper portions thereof, and positioning of apertures 17, causes the appliance to have a low profile with attendant greater comfort to the patient.

Said customization is also intended to ensure that axis 19, which represents the direction of extension of the appliance, will be aligned parallel to the desired vector of distraction, namely parallel to the mandibular transverse occlusal plane. Said alignment is achieved by fitting the appliance, shaped by the precise bending of arms 11 and 12, to the model. When the correct position on the model is verified, a light body P.V.S. (polyvinyl siloxane) or equivalent removable molding composition is applied over the anterior teeth and further extended and shaped laterally to span and embrace the upper portions 15 of said arms. The cured, shaped spanning composition molded onto the appliance represents an "index", designated by numeral 45 in FIG. 6, which defines the precise positioning of the customized appliance. The index is further characterized in having a trough-like portion 46 adapted to fit precisely upon the anterior teeth 47.

A maxillary impression is taken to construct a bite plane, to be utilized during the distraction phase. To determine the amount of distraction needed, a diagnostic setup may be utilized. This may be necessary to determine arch width discrepancies or, to more precisely calculate the amount of crowding and/or protrusion.

The patient is placed in a semi-reclining position. Intravenous general anesthesia is given. Local anesthesia is administered for hemostasis and postoperative pain control. A horizontal incision is made with a #15 blade in the oral mucosa of the lower lip approximately 8 mm. from the mucogingival reflection extending from the right canine tooth to the left canine tooth. The incision is carried through mucosa, submucosa, muscle, and periosteum. A full thickness subperiosteal flap is elevated inferiorly and the symphysis is completely degloved including the inferior border.

The custom designed distraction appliance with attached index is taken to the mouth and seated onto the anterior teeth. The appliance is attached to the bone of the symphysis with two 2.0 millimeter×10millimeter bicortical bone screws 48 through the apertures 17 of the lower (inferior) portions 16. The index is then cut and peeled away from the appliance. Correct positioning of the appliance is checked for the apertures of superior extremities 15. The appliance is then attached to the canine (or other designated tooth) on either side of the planned osteotomy with circumdental 24-gauge stainless steel wire and light-cured resin. A flowable composite, such as Kerr Revolution or Transbond LR, will work well. Superiorly, a tunnel is developed in the midline beneath the attached gingiva up to the gingival margin. A bone bur is used to score the midline of the mandible in a vertical direction. A reciprocating bone saw is then used to create a vertical midline osteotomy 35 out from the inferior border of the mandible up to the apices of the incisor teeth. A narrow osteotome and mallet are used to complete the cut between the roots of the central incisor teeth (or teeth indicated, if a step osteotomy is being performed). The two halves of the mandible are then mobilized. The appliance is activated 2.0 millimeters to ensure adequate separation and mobilization of the osteotomized segments.

The appliance is deactivated after separation and mobilization is confirmed. The wound should be thoroughly irrigated with normal saline solution. Incision closure can be made with multiple interrupted sutures of 4-0 Vicryl material. A pressure dressing is then applied. A 0.12% chlorhexidine oral rinse is prescribed to the patient for 1 week post-operatively.

After a seven-day latency period, the patient is scheduled in the surgeon's office to start the distraction period. Patients are requested to make two 0.5-millimeter activations per day. This is easy for the patient, especially when one complete revolution of barrel 18 yields one millimeter of distraction, corresponding to a one millimeter extrusion of measuring tube 29 from said barrel. For this reason, an arrow which shows direction of rotation appears on one facet 24, and a dot or other indicia appears on an opposite facet, indicating the extent of barrel rotation.

During this phase, it is advisable to see patients every two to three days. Not only will the surgeon ensure that the appliance is being activated, but the total amount of distraction can be determined by inspection of the incremental markings on tube 29. Activation continues in said manner until the desired amount of distraction is achieved.

Once distraction is complete, the anterior portion of the arch wire is cut so that a sectional arch wire can be placed. The purpose of this wire is to support the placement of a pre-selected denture tooth. This will improve cosmetics, as well as, support the dentition, during the consolidation phase.

Following distraction, a flowable bonding compound is applied to machine screw 25 and measuring tube 29 to ensure against any retractive motion of either component. Although there is very little, if any relapse, it is preferable that a slight over-distraction be employed.

The consolidation period will generally vary from eight to twelve weeks. During said period it is preferable to monitor the regenerate through occlusal and periapical x-rays every three to four weeks. The appliance is not removed until bony bridging of the adjacent sides of the osteotomy is seen completed. It is further preferable to see radiographic evidence of the mineralization of the inferior cortex before removal. The removal of the appliance is easily made with local anesthesia and stab incisions.

As seen from P-A cephalometric x-ray, the appliance of this invention produces a parallel regenerate. Thus, there is a proportionate widening of the dento-osseous segments. With basal bone being expanded proportional to the alveolar bone, it is considered that this type of expansion provides greater stability than tooth-borne appliances of the prior art which produce a V-shaped regenerate.

Following the consolidation period of 8 to 12 weeks, the appliance is removed, and post-distraction orthodontic treatment may begin. It is preferred that movement of single rooted teeth into the regenerate should not be initiated for at least 8–12 weeks following distraction. Tooth movement through regenerate bone has been found to occur at a faster rate than through the normal host bone.

While particular examples of the present invention have been shown and described, it is apparent that changes and modifications may be made therein without departing from the invention in its broadest aspects. The aim of the appended claims, therefore, is to cover all such changes and modifications as fall within the true spirit and scope of the invention.

Having thus described my invention, what is claimed is:

1. An intraoral appliance for mandibular widening by symphyseal distraction osteogenesis comprising:
 a) first and second elongated support arms of substantially equal length disposed in facing opposition, each arm comprised of upper and lower aperture-equipped extremities, and a central portion, and
 b) a displacement mechanism disposed between the central portions of said arms and interactive therewith, said mechanism comprising:
  1) a turning barrel elongated upon an axis of rotation between first and second end walls, and having a substantially circular cylindrical exterior surface provided with an annular gripping zone comprised of six flat facets in hexagonal array, said facets having instructive indicia, 2) a machine screw having a proximal extremity attached to said first arm at said central portion and extending in threaded engagement with an axially centered threaded aperture in said first end wall, and terminating in a distal extremity located within said barrel, and 3) a measuring tube slideably emergent from said second end wall upon said axis and extending to a proximal extremity attached to said second arm at said central portion, the distance of emergence of said rod being dependent upon the degree of rotational movement of said barrel.

2. The appliance of claim 1 wherein said support arms are of rigid, yet bendable metal construction.

3. The appliance of claim 2 wherein said support arms are fabricated of stainless steel as monolithic structures.

4. The appliance of claim 3 wherein said support arms are fabricated from wire stock.

5. The appliance of claim 1 wherein the lower portions of said support arms are substantially straight and parallel, and the upper portions of said support arms are divergently directed by virtue of bending.

6. The appliance of claim 5 wherein the divergently directed upper portions of said support arms are bent at an angle of between 90 and 115 degrees with respect to the corresponding lower portions of said support arms.

7. The appliance of claim 1 wherein at least one of said facets has instructional indicia in the form of an arrow which indicates direction of rotation of said turning barrel.

8. The appliance of claim 1 wherein said measuring tube threadably engages internal threading within said turning barrel.

9. The appliance of claim 8 wherein the direction of threaded engagement of said measuring tube with said barrel is opposite to the direction of threaded engagement of said machine screw with said barrel.

10. The appliance of claim 9 wherein said measuring tube has a hollow region and cylindrical outer wall.

11. The appliance of claim 10 wherein a series of millimeter rulings is disposed on the cylindrical outer wall of said measuring tube.

12. The appliance of claim 10 wherein said machine screw is sufficiently narrow to enter said hollow region.

13. The appliance of claim 1 which has been customized to fit a patient by way of bending said arms upon a model of the patient's lower jaw.

14. The appliance of claim 13 wherein said customized appliance contains a removable molded index which spans the apertures of the upper extremities of said support arms and further comprises a trough-like portion adapted to fit precisely upon the patient's anterior teeth.

15. The appliance of claim 14 wherein said index is comprised of a composition which can be easily cut and peeled away by the surgeon after the appliance is attached to the mandibular bone by way of screws engaging the apertures of the lower portions of said support arms.

16. A method for mandibular widening by symphyseal distraction osteogenesis comprising:
　a) pre-surgical orthodontics
　b) installation of the appliance of claim 13
　c) a mid-symphyseal osteotomy
　d) a latency period
　e) a distraction period
　f) a consolidation period, and
　g) post-surgical orthodontics.

\* \* \* \* \*